United States Patent
Martyn et al.

(10) Patent No.: US 6,375,679 B1
(45) Date of Patent: Apr. 23, 2002

(54) PROSTHETIC VALVE SINUS

(75) Inventors: Leat Martyn, Leeds; Clark Colin; Wu Jin, both of Uxbridge, all of (GB)

(73) Assignee: Advanced Medical Solutions Ltd. (GB)

( * ) Notice: Subject to any disclaimer, the term of this patent is extended or adjusted under 35 U.S.C. 154(b) by 0 days.

(21) Appl. No.: 09/463,163

(22) PCT Filed: Jul. 17, 1998

(86) PCT No.: PCT/GB98/01920

§ 371 Date: Mar. 27, 2000

§ 102(e) Date: Mar. 27, 2000

(87) PCT Pub. No.: WO99/03428

PCT Pub. Date: Jan. 28, 1999

(51) Int. Cl.[7] .................................................. A61F 2/24
(52) U.S. Cl. ....................................... 623/2.12; 623/2.15
(58) Field of Search ............................. 623/1.24, 1.25, 623/1.26, 2.17, 2.18, 2.19, 2.13, 2.15, 2.12, 2.14, 2.16

(56) References Cited

U.S. PATENT DOCUMENTS 4,451,936 A * 6/1984 Carpentier et al. ............ 3/1.5
5,037,434 A * 8/1991 Lane ............................. 623/2
5,147,391 A * 9/1992 Lane ............................. 623/2

FOREIGN PATENT DOCUMENTS

GB   2312485    * 10/1997
WO   94/01062   *  1/1994

* cited by examiner

*Primary Examiner*—Corrine McDermott
*Assistant Examiner*—Hieu Phan
(74) *Attorney, Agent, or Firm*—Woodard, Emhardt, Naughton Moriarty & McNett

(57) ABSTRACT

The combination of a prosthetic valve and a sinus. The valve has a plurality of flexible leaflets for opening and closing the valve, each leaflet having an edge region attached to a frame of the valve and further having a free edge. The sinus has a plurality of lobes symmetrically disposed around the periphery of the sinus, and a conduit located downstream of said lobes in the direction of blood flow through the sinus. The sinus is such that the valve may be located therein with said attached edges of any one of the leaflets extending in coincidence with an upstream edge region of a respective lobe, wherein in axial section taken centrally through a lobe.

16 Claims, 2 Drawing Sheets

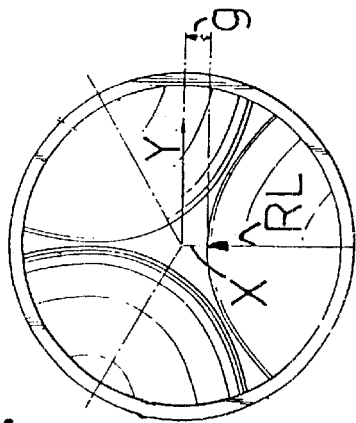
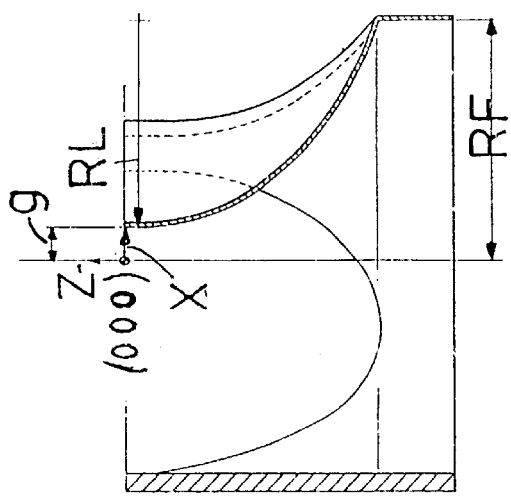
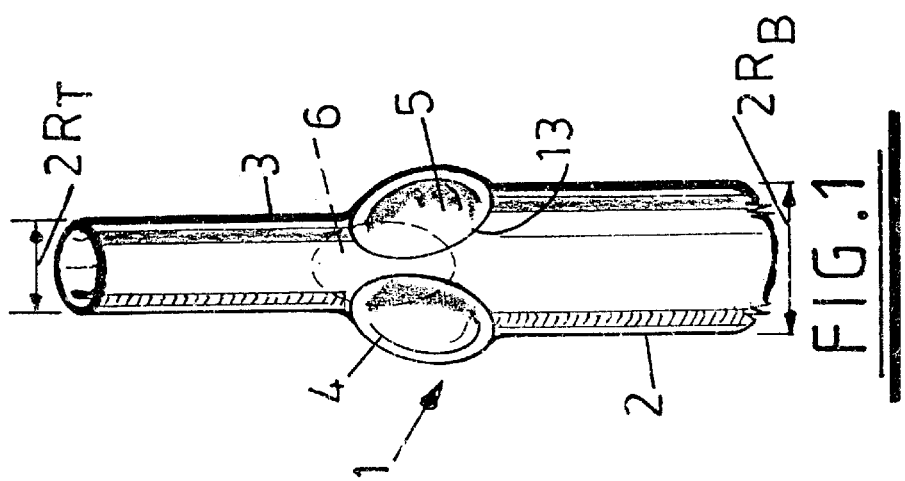

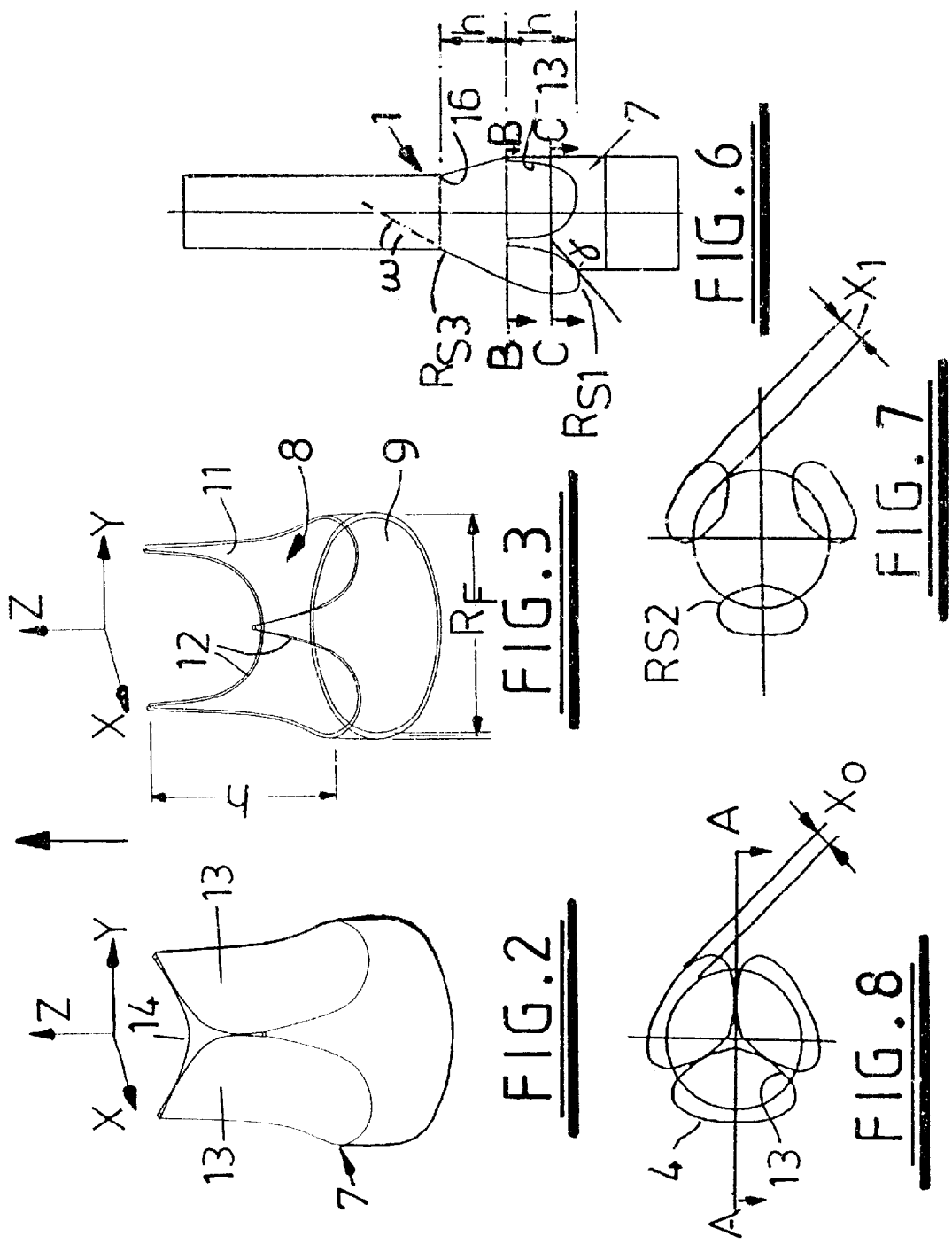

PROSTHETIC VALVE SINUS

BACKGROUND OF THE INVENTION

The present invention relates to a sinus conduit for a prosthetic heart valve and more particularly to a combination of such a sinus conduit and valve that may be used in artificial circulatory equipment which may be employed to assist circulation in patients with impaired heart functions.

DESCRIPTION OF THE RELATED ART

In artificial circulatory equipment, it has been proposed that a prosthetic valve may be enclosed within a structure known as a sinus. Generally the valve will have a plurality of flexible leaflets which serve to open and close the valve to blood flow and the sinus will have a plurality of peripherally disposed lobes located around the leaflets.

There are however disadvantage with existing lobed sinuses in that the shape of the lobes tends to allow blood to accumulate therein with an attendant danger of thrombus formation.

BRIEF SUMMARY OF THE INVENTION

The present invention seeks to obviate or mitigate this disadvantage.

According to the present invention there is provided the combination of (a) a prosthetic valve having a plurality of flexible leaflets for opening and closing the valve and each having an edge region attached to a frame of the valve and further having a free edge, and (b) a sinus having a plurality of lobes symmetrically disposed around the periphery of the sinus, and a conduit (the downstream conduit) located downstream of said lobes in the direction of blood flow through the sinus, the sinus being such that the valve may be located therein with said attached edges of any one of the leaflets extending in coincidence with an upstream edge region of a respective lobe, wherein in axial section taken centrally through a lobe (i) the angle of intersection ($\gamma$) of each leaflet with its respective lobe is from 165 to 195°,
(ii) the radius of curvature of the lobe increases continuously to the downstream end thereof,
(iii) at said downstream end the angle ($\omega$) between notional projection of the inner surface of the lobe into the downstream conduit and the surface of said conduit is 23–37°, and
(iv) the volume of $R_{swp}/R_{ttl}$ (as hereinbefore described) is at least 0.14.

The above defined criteria (i)–(iii) of the lobe ensure that there is continuous movement of blood within the lobe to prevent areas of stagnation and ensure washing of the valve leaflets. More particularly, feature (i) ensures that there is no stagnation of the intersection of the leaflet and the sinus whereas feature (iii) ensures that a portion of the blood issuing as a "jet" from the valve (at least beyond a certain degree of opening thereof) is able to be "deflected" for recirculating motion within the lobe.

Preferably the valve has three leaflets and the sinus is of tri-lobed structure. The valve is preferably of the type disclosed in WO-A-9318721 (The University of Leeds).

The sinus may be of a flexible material, e.g. a biocompatible polyurethane.

Preferably the sinus further comprises an upstream conduit whereby said lobes are located between said upstream and downstream conduits. For preference the internal diameter of the upstream conduit is greater than that of the downstream conduit.

BRIEF DESCRIPTION OF THE DRAWINGS

The invention will be further described by way of example only with reference to the accompanying drawings, in which:

FIG. 1 is a perspective view of one embodiment of sinus;

FIG. 2 shows (to an enlarged scale) a perspective view of one embodiment of heart valve for use in conjunction with the sinus of FIG. 1;

FIG. 3 is a detail of the frame of the valve shown in FIG. 2;

FIG. 4 is a sectional view (to a further enlarged scale) of the valve of FIG. 2 to illustrate various dimensions thereof;

FIG. 5 is a plan view of FIG. 4;

FIG. 6 is a schematic axial sectional view (corresponding to the line A—A in FIG. 8) of a combination of the sinus of FIG. 1 and the valve of FIG. 2;

FIG. 7 is a section on the line C—C of FIG. 6; and

FIG. 8 is a section on the line B—B of FIG. 6.

DETAILED DESCRIPTION OF THE INVENTION

Referring to the drawings, FIG. 1 is a perspective view of one embodiment of sinus 1 in accordance with the invention comprising upstream and downstream circular section conduits 2 and 3 respectively (the latter having an internal radius $R_T$ less than the internal radius $R_B$ of the former) between which is an intermediate section of the sinus formed with three identical lobes 4–6 symmetrically disposed around the sinus periphery.

The sinus 1 is intended for use in conjunction with an artificial heart valve 7 of the type illustrated in more detail in FIGS. 2 and 3. Heart valve 7 is the type disclosed in WO-A-9318721 (The University of Leeds) and comprises a frame 8 (FIG. 3) having a cylindrical lower region 9 (mean radius=$R_F$, wall thickness=$t_F$) from which extend three symmetrically located tapering limbs 11 (see FIG. 2). For the purpose of the later description, the edge region of the frame between the tips of adjacent limbs 11 is referenced as 12 and these tips are at a height h above the lowermost point of edge 12.

Valve 7 incorporates three flexible leaflets 13 each being fixed along the edge 11 between two adjacent limbs 11 and each having a free edge 14. The leaflets form part of a paraboloid of revolution having its axis of revolution lying in a plane orthogonal to the direction of blood flow.

The shape of any one leaflet may be defined by reference to an xyz axis system defined for that leaflet such that the z axis is along the central axis of frame 8, the origin (x=0, y=0, z=0) is at the level of the free edge 14 of the leaflet 13, the x axis bisects the free edge 14 of the leaflet and the y axis is orthogonal to the x and z axes. For such a co-ordinate axis system, the shape of the leaflet is represented by the equation.

$$z^2+y^2=2R_L(x-g)-\alpha(x-g)^2$$

where:

g is the offset of the centre of the free edge 14 of the leaflet 13 from the axis of the frame as shown in FIG. 4;

$R_L$ is the radius of curvature of the leaflet 13 at (g. 0.0) as shown in FIG. 5; and $\alpha$ is a shape parameter and is such that $0<\alpha<1$ Further details as to the structure and mode of operation of the valve are disclosed in WO-A-9318721

Valve 7 is intended to be located within the sinus 1 and for this purpose the radius $R_B$ of the upstream conduit 2 of sinus 1 is equal to $(R_F+t_F/2)$ (i.e. the outer radius of region 9 of heart valve 7). The radius $R_T$ of the downstream conduit 3 of sinus 1 is preferably equal to 0.55 $R_B$ to 0.6$_B$. Between the upstream and downstream conduits 2 and 3 are the identical lobes 4–6 which provide pockets within the sinus 1.

In more detail, each lobe extends over a length of 2 h (h being a dimension of the valve 7 as defined earlier) from the end of upstream conduit 2 and the beginning of downstream conduit 3 (see FIG. 6). Over a distance h from the end of upstream conduit 2, the lobes "protrude" from a region of the sinus having a radius $R_B$ and as viewed in FIG. 7 this region extends between the lowest point of the lobe 4 and section line B—B. Over this region, the peripheral edge 15 of the lobe (i.e. the "junction" of the lobe with that part of the region having radius $R_B$) is of a shape corresponding to that of the edge 12 defined by adjacent limbs 11 of the heart valve 7.

It will be appreciated from the foregoing description that valve 7 is intended to be located within the sinus 1 such that (i) the peripheral edge 13 of each lobe is coincident with a respective edge region 12 of the valve 7 (see FIG. 6) and (ii) the cylindrical region 9 of the valve 7 locates as a close fit within the upstream conduit 2. With the valve 7 so located, each leaflet 13 is able to move for opening and closing of the valve within a respective lobe 4. Furthermore, the distance between the free edges of the leaflets to the upstream end of the downstream conduit is, in the preferred embodiment, equal to h but may more generally be 0.9 h to 1.1 h.

A more detailed description of the shape of the lobes will now be given.

Each lobe 4 is dimensioned such that the maximum height $X_1$ by which the lobe projects (radially) above the outer surface of the upstream conduit (see FIG. 7) is in the range 0.4 $R_F$ to 0.55 $R_F$ and is most preferably about 0.5 $R_F$. At the level of the free edge 13 of the leaflet 12, the height $X_0$ by which the lobe projects above the upstream section of the conduit 2 is from 0.1 $R_F$ to 0.3 $R_F$, preferably about 0.2 $R_F$ (see FIG. 8).

At the base of the leaflet 13, the radius of curvature $R_{S1}$ of the sinus lobe (as viewed in axial section taken centrally through the lobe—see FIG. 6) is from 0.4 $R_F$ to 0.6 $R_F$ ideally 0.5 $R_F$. From this point, the radius of curvature of the lobe continuously increases to a value ($R_{S3}$) at the downstream end of the lobe of from 5 $R_F$ to 5.5 $R_F$ (preferably 5 $R_F$). At the level of the free edge 14 of the leaflet 13, the radius of curvature $R_{S2}$ of the lobe (as viewed in the section of FIG. 8) is from 0.23 $R_F$ to 0.43 $R_F$, preferably about 0.3 $R_F$.

A further feature of the lobe is the angle of intersection of the lobe with the downstream conduit 3. More specifically, when viewed in the axial section of FIG. 6, a notional projection of the inner surface of the lobe forms an angle $\omega$ with the inner surface of the downstream conduit 3 thus defining a ridge 16 at the junction of the lobe and the downstream connula. This angle $\omega$ may be from 23° to 37°, and is more preferably 25° to 35°. Ideally $\omega$ is about 30°.

At the base of the leaflet, there is a smooth transition between the lobe and the leaflet. More specifically, the angle of intersection $\gamma$ (see FIG. 6) between the sinus lobe and the leaflet should be from 165° to 195°, preferably 175 to 185°, and is ideally 180°.

A further feature is the ratio ($R_{swp/ttl}$) of $V_{sweep}$ to $V_{total}$, where
  (i) with the valve located in position in the sinus and the leaflets are closed, $V_{total}$ is the free volume of the sinus between the downstream end of upstream conduit 2 and the upstream end of downstream conduit 3; and
  (ii) $V_{sweep}$ is the leaflet sweeping volume.

The value of $V_{total}$ may be determined by monitoring the leaflets closed, filling the lobe region with a liquid up to the upstream end of the downstream conduit 3 and then measuring the volume of liquid. The value of $V_{sweep}$ may be determined by repeating the foregoing procedure but with the leaflets open and determining the difference between this measured value and $V_{total}$.

The value of $R_{swp/ttl}$ should not be less than 0.14 and is ideally in the range 0.14 to 0.18. Most preferably $R_{swp/ttl}$ is about 0.154.

The above defined criteria for the valve and sinus are summarised in the following table which also includes specific dimensions and angles for a particular combination of sinus and heart valve.

| Variable | Value | Dimension | Description | Drawing No. |
|---|---|---|---|---|
| $R_L$ | — | 6.75 mm | leaflet radius (selected during valve design) | FIG. 4 |
| g | — | 1.2 mm | x coord offset (selected during valve design) | FIG. 4 |
| $\alpha$ | — | 0.5 | alpha variable (selected during valve design) | |
| $R_F$ | — | 9.5 mm | valve frame mean radius (selected during valve design) | FIG. 2 |
| $t_F$ | — | 1.8 mm | valve frame thickness (selected during valve design) | FIG. 2 |
| $R_B$ | $R_F + t_F/2$ | 10.4 mm | radius of upstream sinus section | FIG. 6 |
| $R_T$ | between $0.45R_B$ and $0.6R_B$ | 5.2 mm | radius of downstream sinus section | FIG. 6 |
| h | value of z at y = 0, x = $R_B$ | 12.9 mm | value calculated from valve parabola | FIG. 6 |
| $R_{s1}$ | between $0.4R_F$ and $0.6R_F$ | 5.0 mm | radius of curvature of the sinus lobe at base of leaflet | FIG. 6 |
| $R_{s2}$ | between $0.23R_F$ and $0.43R_F$ | 3.0 mm | radius of curvature of sinus lobe at top of leaflet | FIG. 8 |
| $R_{s3}$ | between $5R_F$ and $5.5R_F$ | 50 mm | radius of sinus lobe at intersection of lobe and downstream section | FIG. 6 |
| $X_0$ | between $0.1R_F$ and $0.3R_F$ | 2.0 mm | height of sinus lobe from upstream section at top of leaflet | FIG. 8 |
| $X_1$ | between $0.4R_F$ and $0.55R_F$ | 5.0 mm | maximum height of sinus from upstream section | FIG. 7 |
| $\gamma$ | between 165–195 pref. 175–185 | 180° | angle of intersection of sinus lobe and leaflet | FIG. 6 |
| $\omega$ | between 23–37° pref. 23–35° | 30° | angle of intersection of sinus lobe and downstream section | FIG. 6 |
| $V_{total}$ | | 6.5 ml | total volume of sinus (including valve) | |
| $V_{sweep}$ | | 1 ml | leaflet sweeping volume | |
| $R_{swp/ttl}$ | 0.14 to 0.18 | 0.154 | Rato $V_{sweep}:V_{total}$ | |

The combination of the sinus 1 and heart valve 7 (assembled in the manner illustrated in FIG. 6) may be used in artificial circulatory equipment. When so used, valve 7 functions in the manner described more fully in WO-A-9318721 but, in brief, flexural opening of leaflets 13 occurs to permit blood to pass through the valve and flexural closure occurs to close the valve. During leaflet opening and closure a number of mechanisms take effect to ensure adequate movement of blood within the lobes and over the surface of the leaflet to prevent thrombus formation. These mechanisms are principally as follows.

1. Entraining Effect of the Ejection Jet

On opening of the valve, a "jet" of blood issues therefrom directed towards the downstream conduit 3. This "jet" causes blood located in the lobes around the outside of the valve to be set in motion.

2. Ejection Jet Deflection

The jet "issuing" from the valve during opening of the leaflets diverges and at a sufficient degree of leaflet opening has, at the entrance to the downstream conduit, a diameter slightly greater than that of the latter. As such, a fraction of the ejecting flow is deflected by the ridge 16 backwardly into a lobe to attach sooner or later to the wall of the lobe and then recirculate therein to drive a vortex on a plane normal to the free edge 14 of the leaflet working within that lobe. In turn, this vortex alters the regional pressure distribution and influences the opening position of the leaflets by balancing the pressure difference across the leaflets.

3. Leaflet Sweeping

Valve leaflet sweeping, which occurs in every pumping cycle during valve opening and closing, gives rise to an increase of momentum in the flow in the lobes. Then amount of this increase is proportional to the ratio $R_{swp/ttl}$.

The effects of these three mechanisms (which may overlap in time) become dominant in early forward flow, peak forward flow and reverse flow respectively.

In the illustrated design of the sinus, the radius $R_T$ of the downstream conduit 3 matches the size of the expanded ejection jet so that unnecessary pressure drop and flow separation around the entrance to the downstream conduit 3 is avoided. The distance been the free edges 14 of the leaflets 13 and the entrance to the conduit 3 is in the preferred embodiment equal to h (the height of the leaflets). This ensures that there is sufficient distance between the free edges of the leaflets and the upstream end of downstream conduit for a recirculating blood flow in the lobes during closure of the leaflets. If this distance is too small (e.g. less than 0.9 h) then there is insufficient recirculating blood flow during leaflet closure. Conversely if this distance is too large then the recirculating flow is too sluggish.

At the ridge 16, a portion of the ejection jet is (on predetermined opening of the leaflets) deflected back into the lobe. This is provided for by appropriate selection of the angle ω which should not be so shallow that there is no deflection nor so steep as to cause the deflected flow to "bounce back" into the ejection jet causing turbulent mixing. Thus the selected value of ω ensures that the desired recirculating motion is set up within the lobe.

Additionally, as described, the radius of curvature of the sinus increases (so viewed in axial section) in a direction going from the upstream conduit 2 to the downstream conduit 3. The minimum value of $R_{S1}$ is sufficiently large such that the angle of transition γ lies between 175° and 185° and is preferably 180°. This ensures a smooth transition between the wall of the sinus lobes and the valve leaflet and that the blood in the region of the "junction" of the base of the leaflet and the wall of the lobe is not able to stagnate.

The abovedescribed mechanisms together ensure that there are no areas of blood stagnation within the sinus and that the leaflets are continuously swept with blood.

What is claimed is:

1. The combination of
   (a) a prosthetic valve having a plurality of flexible leaflets for opening and closing the valve and each having an edge region attached to a frame of the valve and further having a free edge, and
   (b) a sinus having a plurality of lobes symmetrically disposed around the periphery of the sinus, a downstream conduit located downstream of said lobes in the direction of blood flow through the sinus and an upstream conduit located upstream of said lobes in the direction of blood flow through the sinus, the sinus being such that the valve may be located therein with said attached edges of any one of the leaflets extending in coincidence with an upstream edge region of a respective lobe, wherein in axial section taken centrally through a lobe
      (i) the angle of intersection (γ) of each leaflet with its respective lobe is from 165 to 195°,
      (ii) the radius of curvature of the lobe increases continuously to the downstream end thereof,
      (iii) at said downstream end the angle (ω) between notional projection of the inner surface of the lobe into the downstream conduit and the surface of said conduit is 23–37°, and
      (iv) the ratio ($R_{swp/ttl}$) of $V_{sweep}$ to $V_{total}$, where
         (aa) with the valve located in position in the sinus and the leaflets closed $V_{total}$ is the free volume of the sinus between the downstream end of the upstream conduit and the upstream end of the downstream conduit, and
         (bb) $V_{sweep}$ is the leaflet sweeping volume, is at least 0.14.

2. The combination as claimed in claim 1 wherein the leaflets of the valve are substantially identical and each is formed from part of a surface of revolution having its axis of revolution lying in a plane substantially orthognanol to the direction of blood flow through the valve and a shape defined by the equation $$z^2+y^2=2R_L(x-g)-\alpha(x-g)^2$$

where:
   g is the offset of the leaflet from the axis of the frame;
   $R_L$ is the radius of curvature of the leaflet (2) at (g, 0, 0); and
   α is the shape parameter and is greater than 0 and less than 1.

3. The combination as claimed in claim 1 wherein γ is about 175–185°.

4. The combination as claimed in claim 3 wherein γ is about 180°.

5. The combination as claimed in claim 1 wherein ω is 25 to 35°.

6. The combination as claimed in claim 5 wherein ω is about 30°.

7. The combination as claimed in claim 1 wherein $R_{swp}/R_{ttl}$ is about 0.154.

8. The combination as claimed in claim 1 wherein the internal radius ($R_T$ of the downstream conduit is less than the internal radius ($R_B$) of the upstream conduit.

9. The combination as claimed in claim 8 wherein the radius ($R_T$) of the downstream conduit is from 0.45 to 0.6 the radius ($R_B$) of the upstream conduit.

10. The combination as claimed in claim 1 wherein the height ($X_0$) of the sinus lobe from the upstream conduit at the free edge of the leaflet is from 0.1 to 0.3 times the radius ($R_F$) of the frame.

11. The combination as claimed in claim 1 wherein the maximum height ($X_1$) of the lobe from the upstream conduit is from 0.4 to 0.55 times the radius ($R_F$) of the frame.

12. The combination as claimed in claim 1 wherein the lobes extend along the sinus corresponding to a distance of (h+xh) where h is the height of a leaflet and x is 0.9 to 1.1.

13. The combination as claimed in claim 12 wherein the lobes extend along the sinus corresponding to a distance of 2 h.

14. The combination as claimed in claim 1 wherein the radius of curvature ($R_{S1}$) in axial section of the lobe at the base of the leaflet is from 0.4 to 0.6 the radius ($R_F$) of the frame.

15. The combination as claimed in claim 1 wherein the radius of curvature in transverse section of the sinus lobe at the top of the leaflet is from 0.23 to 0.43 the radius ($R_F$) of the frame.

16. The combination as claimed in claim 1 wherein the radius of the sinus lobe in axial section at the intersection of the lobe and the downstream conduit is from 5 to 5.5 times the radius ($R_F$) of the frame.

\* \* \* \* \*

UNITED STATES PATENT AND TRADEMARK OFFICE
CERTIFICATE OF CORRECTION

PATENT NO. : 6,375,679 B1
DATED : April 23, 2002
INVENTOR(S) : Leat Martyn et al.

It is certified that error appears in the above-identified patent and that said Letters Patent is hereby corrected as shown below:

<u>Title page,</u>
Item [75], please replace "Martyn et al." with -- Leat et al. --
In the indication of Inventors, "Leat Martyn, Leeds' Clark Colin, Wu Jin," should be shown as -- Martyn Leat, Leeds; Colin Clark; Jin Wu --.

Signed and Sealed this

First Day of April, 2003

JAMES E. ROGAN
*Director of the United States Patent and Trademark Office*